(12) United States Patent
Nakaji et al.

(10) Patent No.: US 11,534,055 B2
(45) Date of Patent: Dec. 27, 2022

(54) BENDING PORTION FOR ENDOSCOPE, BENDING PIECE OF BENDING PORTION FOR ENDOSCOPE, ENDOSCOPE, AND INJECTION MOLDING MOLD FOR BENDING PIECE OF BENDING PORTION FOR ENDOSCOPE

(71) Applicant: OLYMPUS CORPORATION, Tokyo (JP)

(72) Inventors: Hiroaki Nakaji, Nagoya (JP); Eijiro Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 694 days.

(21) Appl. No.: 16/508,400

(22) Filed: Jul. 11, 2019

(65) Prior Publication Data

US 2019/0328212 A1    Oct. 31, 2019

Related U.S. Application Data (63) Continuation of application No. PCT/JP2017/033772, filed on Sep. 19, 2017.

(30) Foreign Application Priority Data

Feb. 13, 2017   (JP) .............................. JP2017-024216

(51) Int. Cl.
 *A61B 1/005* (2006.01)
 *A61B 1/00* (2006.01)
 *A61B 1/008* (2006.01)

(52) U.S. Cl.
 CPC .......... *A61B 1/0055* (2013.01); *A61B 1/0057* (2013.01); *A61B 1/00071* (2013.01); *A61B 1/008* (2013.01); *A61B 1/0052* (2013.01)

(58) Field of Classification Search
 CPC ..... A61B 1/005; A61B 1/0051; A61B 1/0052; A61B 1/0053; A61B 1/0055; A61B 1/0056; A61B 1/0057; A61B 1/0058; A61B 1/008
 (Continued)

(56) References Cited

U.S. PATENT DOCUMENTS

| 2009/0093680 A1* | 4/2009 | Tsutsumi ............... A61B 1/005 |
| | | 600/140 |
| 2013/0197484 A1* | 8/2013 | Seddon ............. A61M 25/0043 |
| | | 604/533 |

(Continued)

FOREIGN PATENT DOCUMENTS

| CN | 105636494 A | 6/2016 |
| CN | 105873494 A | 8/2016 |

(Continued)

OTHER PUBLICATIONS

International Search Report dated Dec. 12, 2017 issued in PCT/JP2017/033772.

*Primary Examiner* — Ryan N Henderson
(74) *Attorney, Agent, or Firm* — Scully, Scott, Murphy & Presser, P.C.

(57) ABSTRACT

A bending piece of a bending portion for endoscope is provided with: an annular wall portion; a plurality of wire inserting portions in which the wall portion has a first wall thickness; thin wall portions having a second wall thickness thinner than the first wall thickness; and a thick wall portion that is a part of the wall portion different from the thin wall portions between the plurality of wire inserting portions around a longitudinal axis, the thick wall portion formed to have a third wall thickness that is equal to or less than the first wall thickness and is thicker than the second wall thickness.

3 Claims, 8 Drawing Sheets

(58) Field of Classification Search
USPC .......................... 600/139–142; 604/523–528
See application file for complete search history.

(56) References Cited

U.S. PATENT DOCUMENTS

| | | | |
|---|---|---|---|
| 2014/0005683 A1* | 1/2014 | Stand .................... | A61B 34/71 606/130 |
| 2014/0012288 A1* | 1/2014 | Darisse ................ | A61B 1/0055 606/130 |
| 2016/0143633 A1* | 5/2016 | Robert .................. | A61B 50/13 604/95.04 |
| 2016/0213227 A1 | 7/2016 | Osaki et al. | |
| 2016/0235274 A1* | 8/2016 | Graham ................ | A01K 85/00 |
| 2016/0309985 A1 | 10/2016 | Akui | |
| 2016/0310701 A1* | 10/2016 | Pai ..................... | A61B 18/1492 |
| 2016/0316996 A1* | 11/2016 | Nakayama ............ | A61B 1/008 |
| 2019/0328212 A1* | 10/2019 | Nakaji ............... | A61B 1/00131 |

FOREIGN PATENT DOCUMENTS

| | | | | |
|---|---|---|---|---|
| JP | H0654793 | A | 3/1994 | |
| JP | 2003260020 | A | 9/2003 | |
| JP | 2005007068 | A | 1/2005 | |
| JP | 2010220827 | A | 10/2010 | |
| JP | 2011-156269 | A | 8/2011 | |
| JP | 5596838 | B2 | 9/2014 | |
| JP | 2015131015 | A * | 7/2015 | ........... A61B 1/0055 |

\* cited by examiner

FIG. 13

BENDING PORTION FOR ENDOSCOPE, BENDING PIECE OF BENDING PORTION FOR ENDOSCOPE, ENDOSCOPE, AND INJECTION MOLDING MOLD FOR BENDING PIECE OF BENDING PORTION FOR ENDOSCOPE

CROSS REFERENCE TO RELATED APPLICATION

This application is a continuation application of PCT/JP2017/033772 filed on Sep. 19, 2017 and claims benefit of Japanese Application No. 2017-024216 filed in Japan on Feb. 13, 2017, the entire contents of which are incorporated herein by this reference.

BACKGROUND OF THE INVENTION

1. Field of the Invention

The present invention relates to a bending portion for endoscope provided with a plurality of bending pieces having contact portions on end portions facing each other in a longitudinal axis direction, the contact portions being in contact with each other, the plurality of bending pieces being mutually rotatable and being consecutively provided in the longitudinal axis direction; a bending piece of the bending portion for endoscope; an endoscope; and an injection molding mold for a bending piece of a bending portion for endoscope.

2. Description of the Related Art

Recently, endoscopes have been widely used in a medical field and an industrial field. By inserting an elongated insertion portion of an endoscope into a subject/object, observation, treatment and the like of a site to be examined in the subject/object can be performed.

A configuration is well known in which the bending portion for endoscope (hereinafter referred to simply as the bending portion) that is bendable, for example, in a plurality of directions is provided on a distal end side in a longitudinal axis direction (hereinafter referred to simply as the distal end side) of the insertion portion of the endoscope.

In addition to causing progressiveness of the insertion portion in a crooked part of a duct to be improved, the bending portion causes an observation direction of an observation optical system provided on the distal end portion located in front in the longitudinal axis direction of the insertion portion (hereinafter expressed simply as "in front") relative to the bending portion to be changeable.

The bending portion is configured with a plurality of bending pieces, each of which has a predetermined length in the longitudinal axis direction and has an annular wall portion.

As a configuration of the bending portion, a configuration is well known in which the bending portion is bendable in four directions of up, down, left and right by bending pieces adjoining in the longitudinal axis direction, among the plurality of bending pieces, being coupled with each other via a plurality of rotatable rivets causing the bending portion to bend in the up and down directions or a plurality of rotatable rivets causing the bending portion to bend in the left and right directions.

More specifically, a configuration is well known in which the bending portion is bendable in the four directions of up, down, left and right by alternately using first rivets and second rivets in the longitudinal axis direction to couple the plurality of bending pieces in the longitudinal axis direction in such a manner that, for bending pieces adjoining in the longitudinal axis direction, a first bending piece and a second bending piece are coupled via a pair of first rivets, the second bending piece and a third bending piece are coupled via a pair of second rivets located being displaced from the first rivets by 90° around a longitudinal axis of the bending portion, the third bending piece and a fourth bending piece are coupled via a pair of first rivets, the fourth bending piece and a fifth bending piece are coupled with a pair of second rivets.

Note that, in the insertion portion, two pairs of wires, that is, four wires movable back and forth in the longitudinal axis direction in a manner that the pairs of wires face each other, with a central axis of the plurality of bending pieces parallel to the longitudinal axis direction between the pairs of wires, distal ends in the longitudinal axis direction (hereinafter referred to simply as the distal ends) of the four wires being fixed to a bending piece located at a most distal end side among the plurality of bending pieces.

By any of the four pulling wires (hereinafter referred to simply as the wires) being pull-operated from the operation portion of the endoscope, the bending portion can bend in any of the up, down, left and right directions.

As for the bending portion, a configuration is also well known in which bending pieces adjoining in the longitudinal axis direction are coupled via a pair of first rivets or a pair of second rivets, and the bending portion can bend in two directions, the up and down directions or the left and right directions, by a pair of wires, that is, two wires inserted in the insertion portion.

In a configuration of an endoscope used in the medical field in which an insertion portion with a small diameter not more than 5 mm or 3 mm, for example, like an insertion portion of a nephroscope is required, the two-direction bending structure is mainly adopted for a bending portion because of restriction of an outer diameter of the bending portion.

However, operability of the endoscope is improved if the bending operation has the four-direction bending structure. Therefore, there is a request for adopting the four-direction bending structure for the bending portion.

In order to achieve a reduced diameter of the bending portion, Japanese Patent Application Laid-Open Publication No. 2005-7068 discloses a configuration of a bending portion having a rivetless structure in which a plurality of bending pieces are consecutively provided in a longitudinal axis direction, the plurality of bending pieces having contact portions provided on end portions facing each other in a longitudinal axis direction, the end portions being in contact with each other and the plurality of bending pieces being mutually rotatable, and four wires pass through an annular wall portion of each bending piece.

SUMMARY OF THE INVENTION

A bending portion for endoscope according to one aspect of the present invention is a bending portion for endoscope including a plurality of bending pieces having contact portions on end portions facing in a longitudinal axis direction, the contact portions being in contact with each other, the plurality of bending pieces being mutually rotatable and being consecutively provided in the longitudinal axis direction, wherein each of the bending pieces includes: an annular wall portion having an inner peripheral surface and an outer peripheral surface formed around a longitudinal axis and having a predetermined length in the longitudinal axis direction; a plurality of wire inserting portions in which the wall portion has a first wall thickness and through holes are formed, the through holes passing through the wall portion in the longitudinal axis direction, pulling wires configured to cause the bending pieces to rotate being inserted through the through holes; thin wall portions having a second wall thickness thinner than the first wall thickness on the wall portion between the plurality of wire inserting portions around the longitudinal axis; and a thick wall portion that is a part of the wall portion different from the thin wall portions between the plurality of wire inserting portions around the longitudinal axis, the thick wall portion being formed to have a third wall thickness that is equal to or less than the first wall thickness and is thicker than the second wall thickness.

A bending portion for endoscope according to another aspect of the present invention is a bending portion for endoscope including a plurality of bending pieces having contact portions on end portions facing each other in a longitudinal axis direction, the contact portions being in contact with each other, the plurality of bending pieces being mutually rotatable and being consecutively provided in the longitudinal axis direction, wherein each of the bending pieces includes: an annular wall portion having an inner peripheral surface and an outer peripheral surface formed around a longitudinal axis and having a predetermined length in the longitudinal axis direction; a plurality of wire inserting portions in which the wall portion has a first wall thickness and through holes are formed, the through holes passing through the wall portion in the longitudinal axis direction, pulling wires configured to cause the bending pieces to rotate being inserted through the through holes; thin wall portions having a second wall thickness thinner than the first wall thickness on the wall portion between the plurality of wire inserting portions around the longitudinal axis; and a thick wall portion that is a part of the wall portion different from the thin wall portions between the plurality of wire inserting portions around the longitudinal axis, the thick wall portion being formed to have a third wall thickness that is thicker than the second wall thickness; wherein a gate mark of injection molding for molding the bending piece is formed on the thick wall portion.

A bending piece of a bending portion for endoscope according to one aspect of the present invention is provided with: an annular wall portion having an inner peripheral surface and an outer peripheral surface formed around a longitudinal axis and having a predetermined length in a longitudinal axis direction; a plurality of wire inserting portions in which the wall portion has a first wall thickness and through holes are formed, the through holes passing through the wall portion in the longitudinal axis direction and allowing insertion of pulling wires; thin wall portions having a second wall thickness thinner than the first wall thickness on the wall portion between the plurality of wire inserting portions around the longitudinal axis; and a thick wall portion that is a part of the wall portion different from the thin wall portions between the plurality of wire inserting portions around the longitudinal axis, the thick wall portion being formed to have a third wall thickness that is equal to or less than the first wall thickness and is thicker than the second wall thickness.

An endoscope according to one aspect of the present invention includes the bending pieces of a bending portion for endoscope described above.

An injection molding mold for a bending piece of a bending portion for endoscope according to one aspect of the present invention is an injection molding mold for a bending piece of a bending portion for endoscope; the bending piece including: an annular wall portion having an inner peripheral surface and an outer peripheral surface formed around a longitudinal axis and having a predetermined length in a longitudinal axis direction; a plurality of wire inserting portions in which the wall portion has a first wall thickness and through holes are formed, the through holes passing through the wall portion in the longitudinal axis direction and allowing insertion of pulling wires; thin wall portions having a second wall thickness thinner than the first wall thickness on the wall portion between the plurality of wire inserting portions around the longitudinal axis; and a thick wall portion that is a part of the wall portion different from the thin wall portions between the plurality of wire inserting portions around the longitudinal axis, the thick wall portion being formed to have a third wall thickness that is thicker than the second wall thickness; wherein a gate or an eject pin for injection molding is positioned at a position where a surface of an end portion of the thick wall portion in the longitudinal axis direction is formed.

DETAILED DESCRIPTION OF THE PREFERRED EMBODIMENT(S)

An embodiment of the present invention will be described with reference to drawings. Note that it should be noticed that the drawings are schematic, and a relationship between thickness and width of each member, a thickness ratio among respective members and the like are different from actual ones, and it goes without saying that, among the drawings, portions that are different in mutual dimensional relationship and ratio are included.

Figure 1:
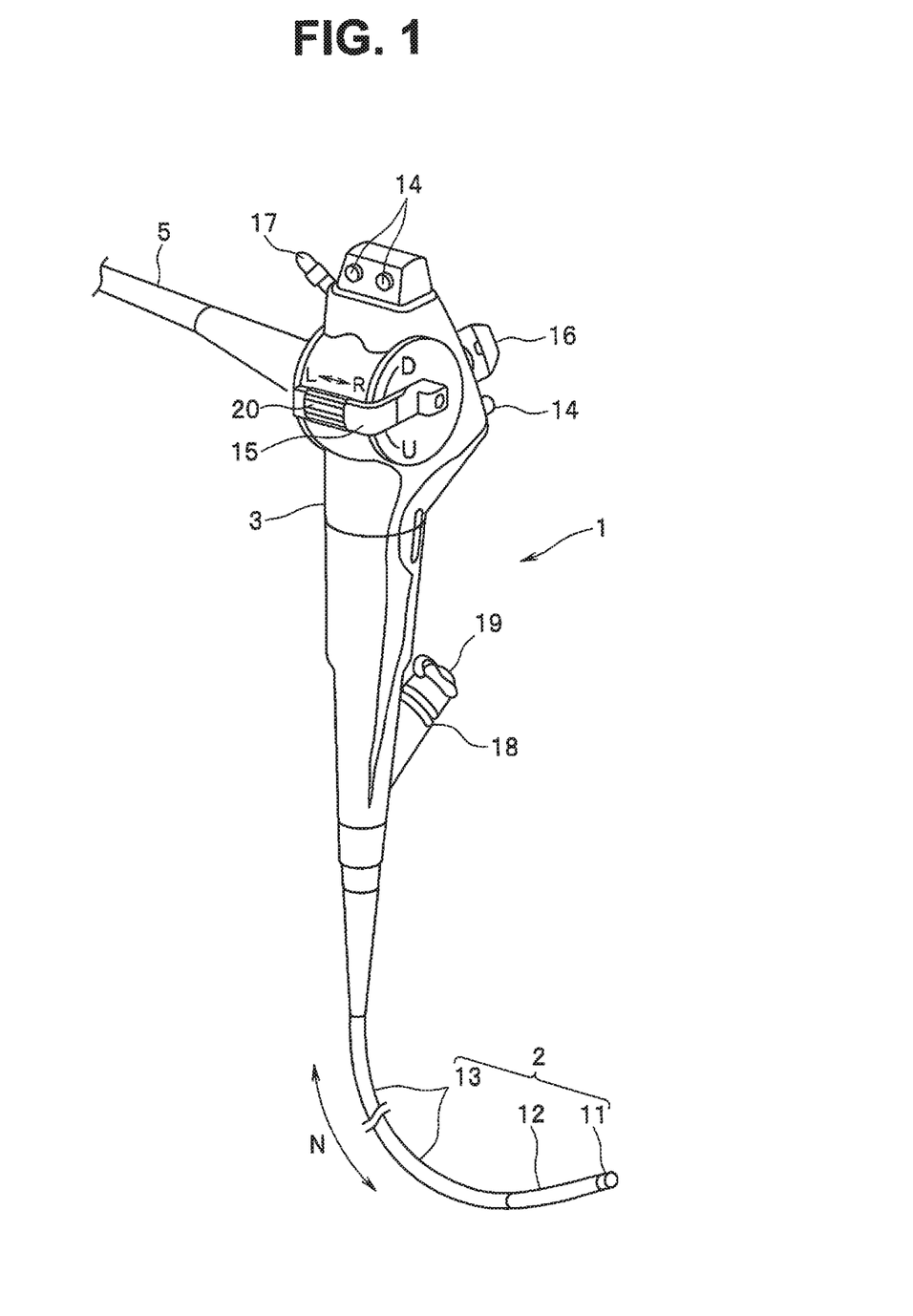
FIG. 1 is a partial perspective view showing an endoscope provided with a bending portion of the present embodiment in an insertion portion.

FIG. 1 is a partial perspective view showing an endoscope, an insertion portion of which is provided with a bending portion of the present embodiment. As shown in FIG. 1, a main part of an endoscope 1 is configured with an insertion portion 2 that is elongated in a longitudinal axis direction N and has flexibility, an operation portion 3 provided on a proximal end side in the longitudinal axis direction N (hereinafter referred to simply as the proximal end side) of the insertion portion 2, a universal cord 5 extending from the operation portion 3 and a connector not shown, the connector being provided on an extension end of the universal cord and connected to an image processing apparatus, an optical source apparatus and the like that are not shown.

A main part of the insertion portion 2 is configured with a rigid distal end portion 11 provided with an observation optical system and the like inside, the observation optical system and the like not being shown, a bending portion 12 bendable in a plurality of directions, for example, four directions of up, down, left and right, which is provided on a proximal end side of the distal end portion 11, and a flexible tube portion 13 having flexibility, which is provided on a proximal end side of the bending portion 12 in the order from a distal end side.

On a proximal end side of the operation portion 3, a remote switch 14 for giving image control instructions such as freeze and release, bending operation levers 15 and 20 for performing bending operation of the bending portion 12, a suction button 16 for performing a suction operation, a suction pipe sleeve 17 communicating with a suction channel 80 (see FIG. 6) to be described later, the suction channel 80 being provided in the insertion portion 2, and the like are provided.

Furthermore, a treatment instrument insertion port 18 for inserting a treatment instrument such as forceps into the suction channel 80 is provided on a distal end side of the operation portion 3, and a forceps plug 19 is attachable to and detachable from the treatment instrument insertion port 18.

Figure 2:
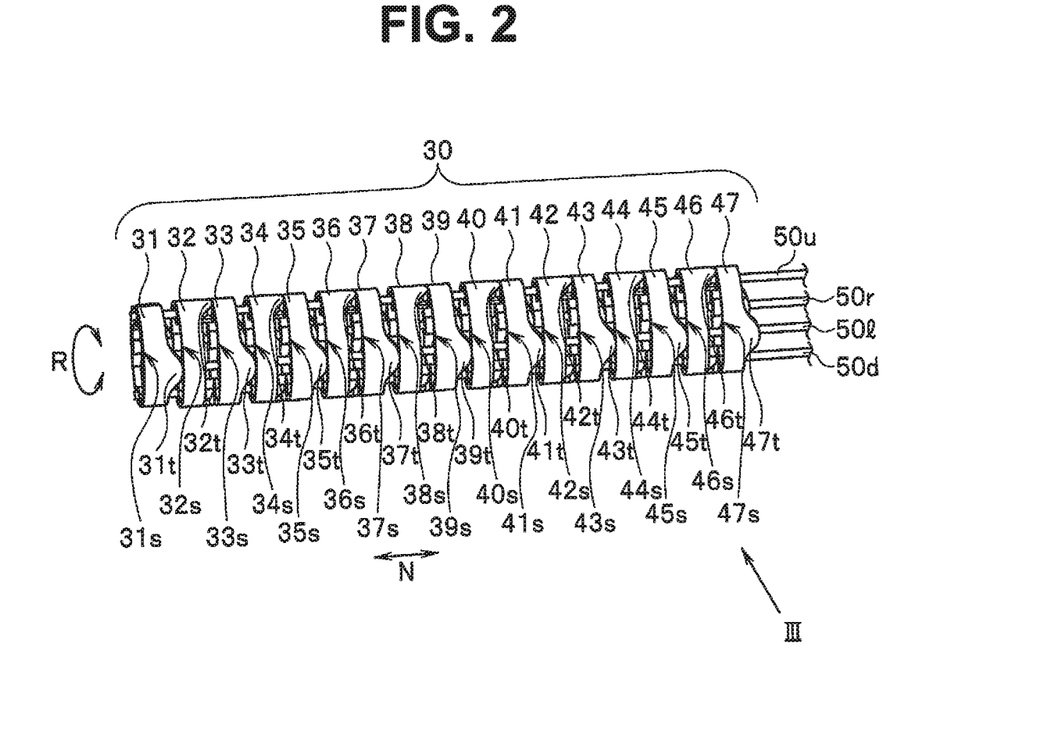
FIG. 2 is a perspective view showing a plurality of bending pieces constituting the bending portion in FIG. 1 together with four wires.
Figure 3:
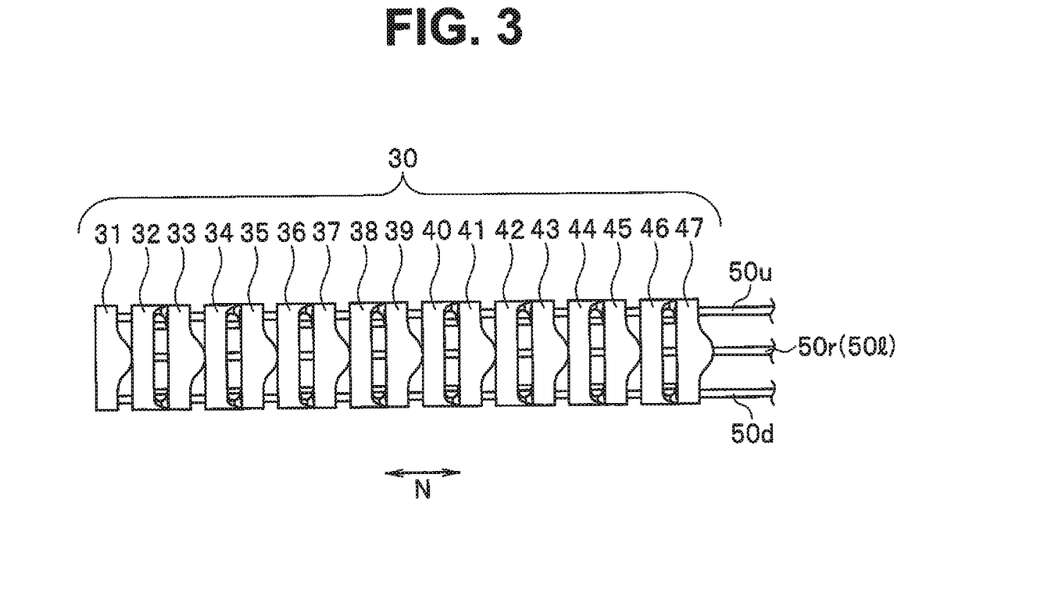
FIG. 3 is a side view in which the plurality of bending pieces and the four wires in FIG. 2 are seen from a direction III in FIG. 2.
Figure 4:
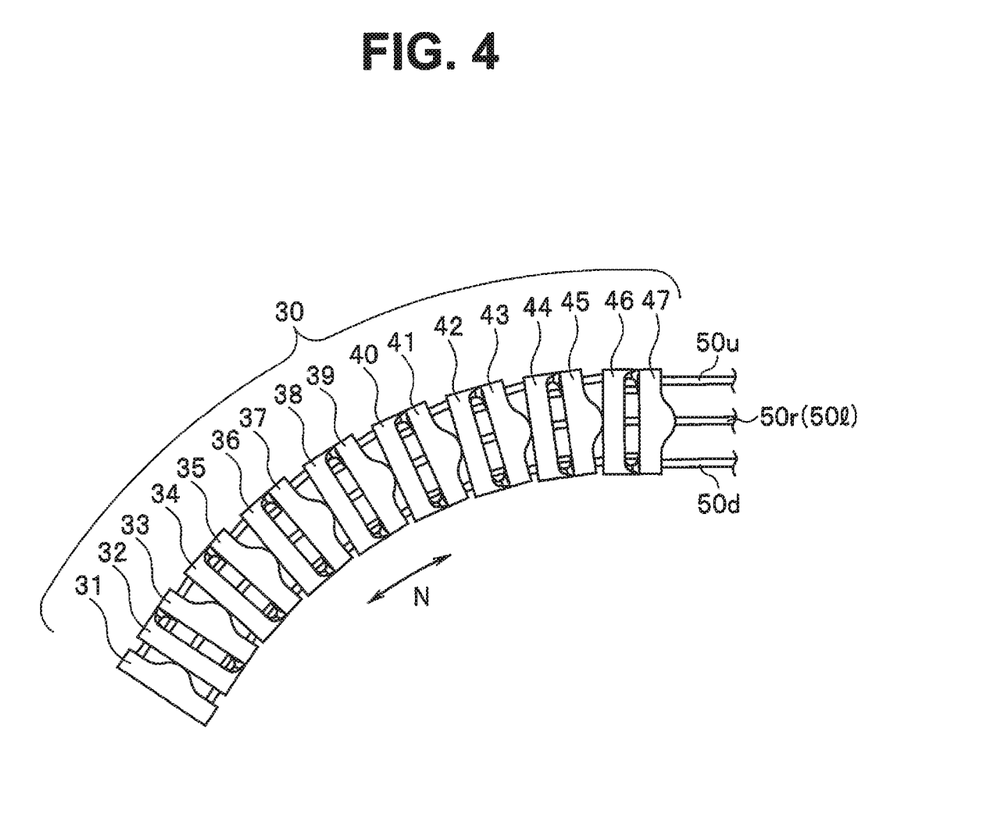
FIG. 4 is a side view showing a state in which the plurality of bending pieces in FIG. 3 bend in one direction by any one of the four wires being pulled.

Next, a configuration of the bending portion 12 will be shown with FIGS. 2 to 4. FIG. 2 is a perspective view showing a plurality of bending pieces constituting the bending portion in FIG. 1 together with four wires; FIG. 3 is a side view in which the plurality of bending pieces and the four wires in FIG. 2 are seen from a direction III in FIG. 2; and FIG. 4 is a side view showing a state in which the plurality of bending pieces in FIG. 3 bend in one direction by any one of the four wires being pulled.

As shown in FIGS. 2 to 4, in the present embodiment, the bending portion 12 is configured with a plurality of bending pieces 31 to 47 being consecutively provided in the longitudinal axis direction N.

Note that though a case where seventeen bending pieces are consecutively provided in a longitudinal axis direction is shown as an example in FIGS. 2 to 4, the number of bending pieces is not limited to seventeen.

On proximal end surfaces of the plurality of bending pieces 31 to 47, which are end portions in the longitudinal axis direction N, pairs of protruding portions 31*t* to 47*t*, which extend backward in the longitudinal axis direction N (hereinafter referred to simply as backward) and which are contact portions symmetrical about central axes of the plurality of bending pieces 31 to 47, are formed, respectively.

Note that the pairs of protruding portions 31*t* to 47*t* are each arranged in such a manner that they are displaced by about 90° in a direction-around-longitudinal-axis R relative to a pair of protruding portions of a bending piece adjoining in the longitudinal axis direction N.

More specifically, the pair of protruding portions 32*t* is arranged in such a manner that they are displaced by about 90° in the direction-around-longitudinal-axis R relative to the pair of protruding portions 31*t*; the pair of protruding portions 33*t* is arranged in such a manner that they are displaced by about 90° in the direction-around-longitudinal-axis R relative to the pair of protruding portions 32*t*; the pair of protruding portions 34*t* is arranged in such a manner that they are displaced by about 90° in the direction-around-longitudinal-axis R relative to the pair of protruding portions 33*t*; and the like. Thus, the pairs of protruding portions 31*t* to 47*t* are each arranged in such a manner that they are displaced by about 90° in the direction-around-longitudinal-axis R relative to a pair of protruding portions of a bending piece adjoining in the longitudinal axis direction N.

Note that the pairs of protruding portions 31*t* to 47*t* are not necessarily required to be arranged in such a manner that they are displaced by about 90° in the direction-around-longitudinal-axis R relative to a pair of protruding portions of a bending piece adjoining in the longitudinal axis direction N. For example, such a form can be also adopted that the protruding portions 31*t* and 32*t* are not mutually displaced in the direction-around-longitudinal-axis R, but the protruding portions 33*t* are displaced from the protruding portions 32*t* by 90° in the direction-around-longitudinal-axis R.

Therefore, the pairs of protruding portions 31*t*, 33*t*, 35*t*, 37*t*, 39*t*, 41*t*, 43*t*, 45*t* and 47*t* are arranged at the same positions in the direction-around-longitudinal-axis R, and the pairs of protruding portions 32*t*, 34*t*, 36*t*, 38*t*, 40*t*, 42*t*, 44*t* and 46*t* are arranged at the same positions in the direction-around-longitudinal-axis R.

The pairs of protruding portions 31*t* to 46*t* are in contact with distal end surfaces 32*s* to 47*s*, which are contact portions provided on longitudinal-axis-direction end portions of bending pieces adjoining in the longitudinal axis direction N, respectively.

More specifically, the pair of protruding portions 31*t* is in contact with the distal end surface 32*s*, the pair of protruding portions 32*t* is in contact with the distal end surface 33*s*, the pair of protruding portions 33*t* is in contact with the distal end surface 34*s*; and the like. Thus, the plurality of pairs of protruding portions 31*t* to 46*t* are in contact with the distal end surfaces 32*s* to 47*s* adjoining in the longitudinal axis direction N, respectively.

Consequently, the plurality of bending pieces 31 to 47 are configured to be mutually rotatable relative to the bending pieces adjoining in the longitudinal axis direction N, respectively.

More specifically, the bending pieces 31 and 32 are in contact with each other in a manner of being rotatable in the up and down directions in FIGS. 2 to 4: the bending pieces 32 and 33 are in contact with each other in a manner of being rotatable in the left and right directions in FIGS. 2 to 4; the bending pieces 33 and 34 are in contact with each other in the manner of being rotatable in the up and down directions in FIGS. 2 to 4; the bending pieces 34 and 35 are in contact with each other in the manner of being rotatable in the left and right directions in FIGS. 2 to 4; and the like. Thus, the plurality of bending pieces 31 to 47 are configured to be mutually rotatable relative to the bending pieces adjoining in the longitudinal axis direction N, respectively.

Therefore, as shown in FIG. 4, for example, when a wire 50*d* to be described later is pulled backward, the bending piece 31 rotates downward via the pair of protruding portions 31*t* that is in contact with the distal end surface 32*s*; the bending piece 33 rotates downward via the pair of protruding portions 33*t* that is in contact with the distal end surface 34*s*; the bending piece 35 rotates downward via the pair of protruding portions 35*t* that is in contact with the distal end surface 36*s*; the bending piece 37 rotates downward via the pair of protruding portions 37*t* that is in contact with the distal end surface 38*s*; the bending piece 39 rotates downward via the pair of protruding portions 39*t* that is in contact with the distal end surface 40*s*; the bending piece 41 rotates downward via the pair of protruding portions 41*t* that is in contact with the distal end surface 42*s*; the bending piece 43 rotates downward via the pair of protruding portions 43*t* that is in contact with the distal end surface 44*s*; the bending piece 45 rotates downward via the pair of protruding portions 45*t* that is in contact with the distal end surface 46*s*; and, thereby, the bending portion 12 bends downward in FIG. 4.

Note that when a wire 50*u* to be described later is pulled backward, the bending portion 12 bends upward in FIG. 4 by each of the bending pieces 31, 33, 35, 37, 39, 41, 43 and 45 rotating upward contrary to the above.

Further, for example, when a wire 50*r* to be described later is pulled backward, the bending piece 32 rotates in the right direction via the pair of protruding portions 32*t* that is in contact with the distal end surface 33*s*; the bending piece 34 rotates in the right direction via the pair of protruding portions 34*t* that is in contact with the distal end surface 35*s*; the bending piece 36 rotates in the right direction via the pair of protruding portions 36*t* that is in contact with the distal end surface 37*s*; the bending piece 38 rotates in the right direction via the pair of protruding portions 38*t* that is in contact with the distal end surface 39*s*; the bending piece 40 rotates in the right direction via the pair of protruding portions 40*t* that is in contact with the distal end surface 41*s*; the bending piece 42 rotates in the right direction via the pair of protruding portions 42*t* that is in contact with the distal end surface 43*s*; the bending piece 44 rotates in the right direction via the pair of protruding portions 44*t* that is in contact with the distal end surface 45*s*; the bending piece 46 rotates in the right direction via the pair of protruding portions 46*t* that is in contact with the distal end surface 47*s*; and, thereby, the bending portion 12 bends in the right direction in FIG. 4.

Note that when a wire 50*l* to be described later is pulled backward, the bending portion 12 bends in the left direction in FIG. 4 by each of the bending pieces 32, 34, 36, 38, 40, 42, 44 and 46 rotating in the left direction contrary to the above.

In other words, the bending portion 12 of the present embodiment has a known rivetless structure in which rivets are not used for mutual coupling among the plurality of bending pieces 31 to 47.

Next, a configuration of each of the plurality of bending pieces 31 to 47 will be described with FIGS. 5 to 7 by taking the bending piece 33 as an example.

Figure 5:
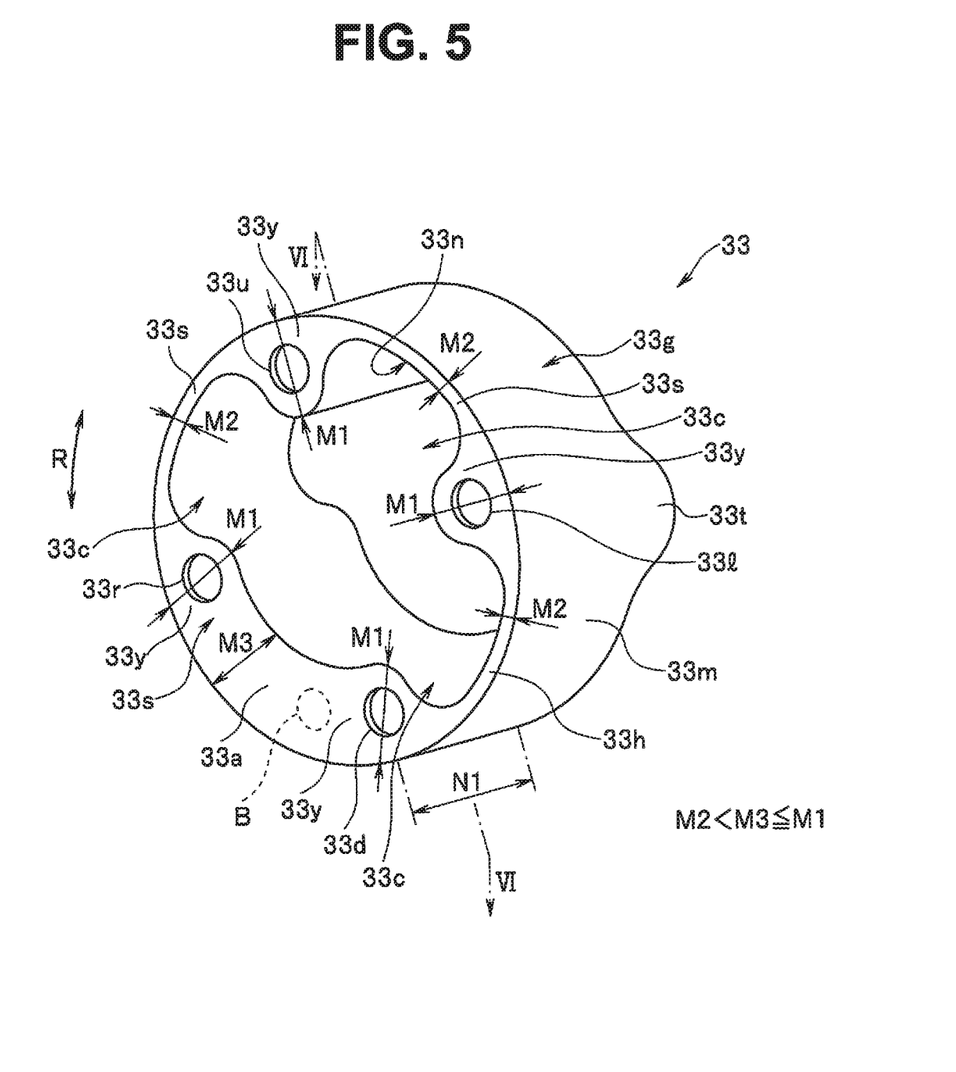
FIG. 5 is an enlarged perspective view of one of the plurality of bending pieces in FIG. 2.

FIG. 5 is an enlarged perspective view of one of the plurality of bending pieces in FIG. 2; FIG. 6 is a cross-sectional view of the bending piece along a VI-VI line in FIG. 5; and FIG. 7 is a cross-sectional view of a conventional bending piece.

Figure 6:
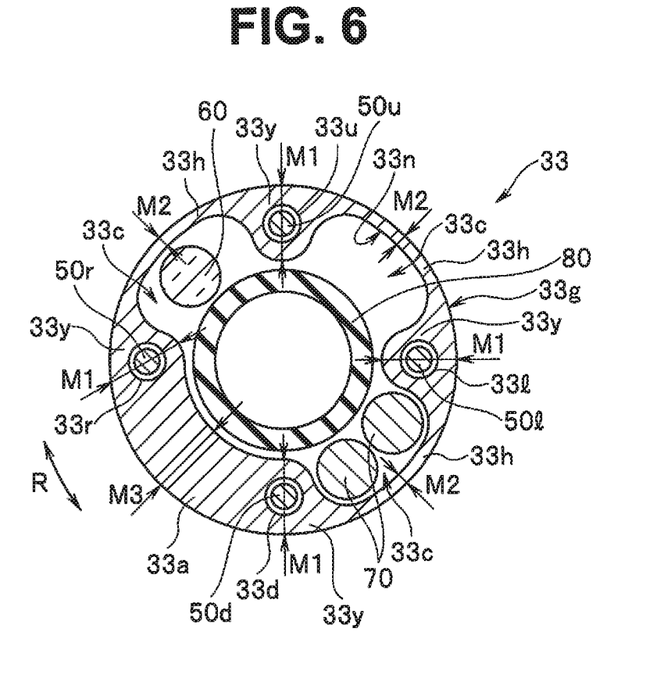
FIG. 6 is a cross-sectional view of the bending piece along a VI-VI line in FIG. 5.

As shown in FIGS. 5 and 6, in the present embodiment, the bending piece 33 has an inner peripheral surface 33*n* and an outer peripheral surface 33*g* formed in the direction-around-longitudinal-axis R and is provided with an annular wall portion 33*m* having a predetermined length N1 in the longitudinal axis direction N.

The wall portion 33*m* is formed with metal, for example, SUS630 or 316L, by MIM (Metal Injection Molding) molding. Note that the wall portion 33*m* may be injection-molded with resin.

As shown in FIG. 6, the suction channel 80 described above is inserted almost in a center of a space surrounded by the inner peripheral surface 33*n* of the wall portion 33*m*.

The wall portion 33*m* is provided with four wire inserting portions 33*y* in the longitudinal axis direction N, for example, being sequentially displaced by about 90° in the direction-around-longitudinal-axis R, where through holes 33*u*, 33*d*, 33*r* and 33*l* which pass through the wall portion 33*m* in the longitudinal axis direction N and in which the four wires 50*u*, 50*d*, 50*r* and 50*l* causing the plurality of bending pieces 31 to 47 to rotate by pulling are formed and where the wall portion 33*m* has a first wall thickness M1.

On the wall portion 33*m* between the plurality of wire inserting portions 33*y* in the direction-around-longitudinal-axis R, thin wall portions 33*h* having a second wall thickness M2 thinner than the first wall thickness M1 (M2<M1) is formed in the longitudinal axis direction N. Note that, as the second wall thickness M2, for example, 0.2 mm or less is given.

As shown in FIG. 6, spaces 33*c* of the bending piece 33, which face the inner peripheral surface 33*n* of the thin wall portions 33*h* and exist between the inner peripheral surface 33*n* and an outer peripheral surface of the suction channel 80 constitute an accommodating portion configured to accommodate internal components such as a light guide 60, an image pickup cable 70 and the like which are long items extending in the longitudinal axis direction N.

Figure 7:
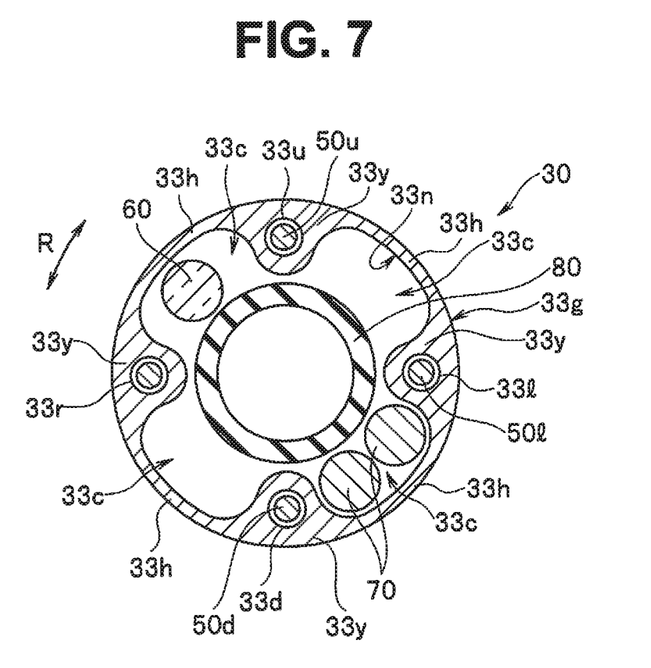
FIG. 7 is a cross-sectional view of a conventional bending piece.

Note that it is the same as a conventional bending piece as shown in FIG. 7 that the wall portion 33*m* has the plurality of wire inserting portions 33*y* and the thin wall portions 33*h* and that the spaces 33*c* constitute accommodating portions.

Here, as shown in FIGS. 5 and 6, on a part of the wall portion 33*m* different from the thin wall portions 33*h* between the plurality of wire inserting portions 33*y* in the direction-around-longitudinal-axis R, more specifically, on an area of the wall portion 33*m* that does not influence arrangement of the internal components, a thick wall portion 33*a* having a third wall thickness M3 that is thicker than the second wall thickness M2 and is equal to or thinner than the first wall thickness M1 (M2<M3≤M1) is formed in the longitudinal axis direction N.

Between adjoining bending pieces, thick wall portions are formed at corresponding positions in the direction-around-longitudinal-axis R.

Note that since each of the pairs of protruding portions 31*t* to 47*t* are arranged being displaced by about 90° in the direction-around-longitudinal-axis R relative to a pair of protruding portions of a bending piece adjoining in the longitudinal axis direction N, the thick wall portions of the bending pieces 32, 34, 36, 38, 40, 42, 44 and 46 are formed at positions being displaced by about 90° in the direction-around-longitudinal-axis R relative to the thick wall portions of the bending pieces 31, 33, 35, 37, 39, 41, 43, 45 and 47, and, at the time of assembly, the positions in the direction-around-longitudinal-axis R correspond to one another.

Therefore, for each of the bending pieces 31, 33, 35, 37, 39, 41, 43, 45 and 47, the wire 50*u* is inserted through the through hole 33*u*, the wire 50*d* is inserted through the through hole 33*d*, the wire 50*r* is inserted through the through hole 33*r*, and the wire 50*l* is inserted through the through hole 33*l*. For each of the bending pieces 32, 34, 36, 38, 40, 42, 44 and 46, however, the wires 50*u* and 50*d* are inserted in either the through hole 33*r* or 33*l*, and the wires 50*r* and 50*l* are inserted in either the through hole 33*u* or 33*d*.

Furthermore, as shown in FIG. 5, on the distal end surface 33*s*, which is an end surface of the thick wall portion 33*a* in the longitudinal axis direction N, a gate mark B after injection molding for forming the bending piece 33 is formed. Note that the gate mark B is configured with a protruding portion that is projectingly provided on the distal end surface 33*s*.

A push-out portion used at the time of pushing the bending piece 33 out of a mold with an eject pin after MIM molding may be provided on the distal end surface 33*s* though it is not shown.

Note that other components of the bending piece 33 are similar to components of a bending piece used for a conventional rivetless bending portion structure. The above configuration of the bending piece 33 applies to all of the bending pieces 31, 32, and 34 to 47.

Thus, in the present embodiment, it has been shown that, on a part of a wall portion of each of the bending pieces constituting the bending portion 12 that is different from thin wall portions 33*h* between the plurality of wire inserting portions 33*y* in the direction-around-longitudinal-axis R, a thick wall portion having the third wall thickness M3 that is thicker than the second wall thickness M2 and is equal to or thinner than the first wall thickness M1 (M2<M3≤M1) is formed in the longitudinal axis direction N.

According to the above, since the thick wall portion is formed on an area of the wall portion of each of the bending pieces that does not influence arrangement of the internal components, it becomes easy to pour metal powder into a mold at the time of performing MIM molding of the bending piece. Therefore, fillability of the metal powder is improved, and it is possible to perform MIM molding of the bending piece into a form having thin wall portions at a low cost.

Since the thick wall portion is formed on the area of the wall portion that does not influence arrangement of the internal components, an outer diameter of the bending piece is not influenced even if the thick wall portion is provided on the wall portion. Therefore, it is possible to maintain thinning of the wall of the bending piece.

Furthermore, in the present embodiment, it has been shown that the gate mark B is formed on a distal end surface of the thick wall portion of each of the bending pieces.

According to the above, since the gate mark B is formed on the distal end surface of the thick wall portion of each of the bending pieces, the gate mark B does not hinder bending even if deburring of the gate mark B is not performed after molding of the bending pieces as shown in FIGS. 2 to 4.

Therefore, a process for deburring the gate mark B becomes unnecessary, and it is possible to reduce manufacturing cost of the bending pieces. In addition, it is possible to prevent the thin wall portions from deforming accompanying deburring.

In the present embodiment, it has also been shown that a push-out portion is provided on the distal end surface of the thick wall portion.

According to the above, though there is a possibility that, if the push-out portion is provided on a distal end surface of a thin wall portion as shown in FIG. 7, the thin wall portion deforms at the time of pushing the bending piece 33 out of a mold with an eject pin, it is possible to, if the push-out portion is provided on the distal end surface of the thick wall portion as in the present embodiment, prevent the deformation at the time of pushing out.

From the above, it is possible to provide a bending portion for endoscope configured with bending pieces formed at a low cost and having a diameter-reduced rivetless structure.

Figure 8:
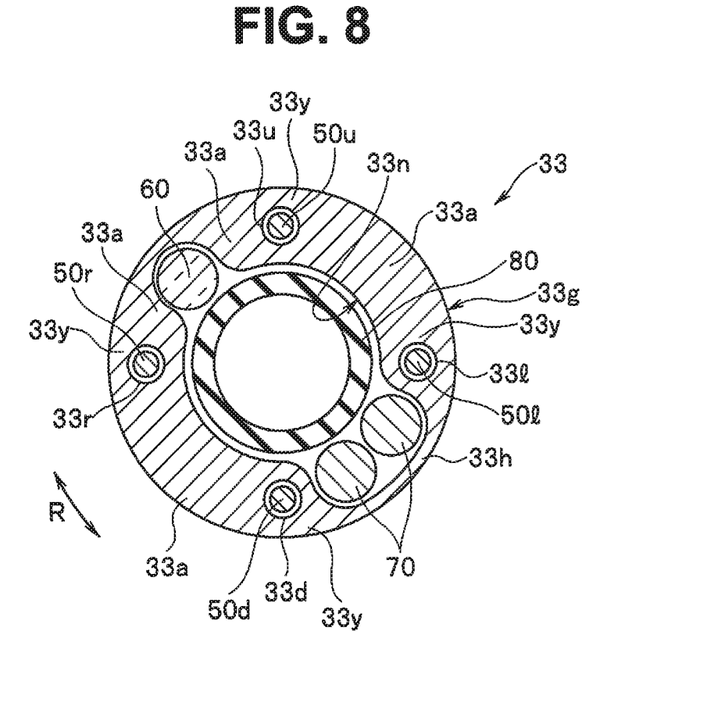
FIG. 8 is a cross-sectional view of a wall portion showing a modification of a thick wall portion in FIG. 6.
Figure 9:
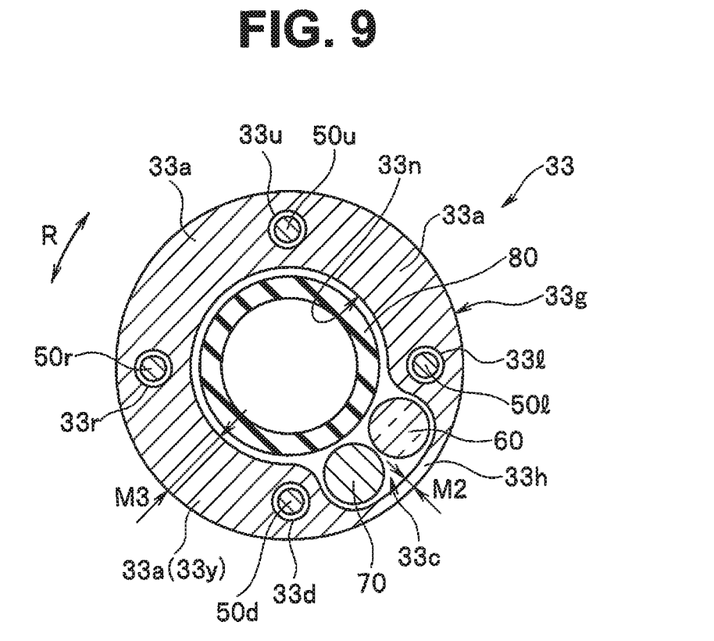
FIG. 9 is a cross-sectional view of a wall portion showing a modification of the thick wall portion different from FIGS. 6 and 8.
Figure 10:
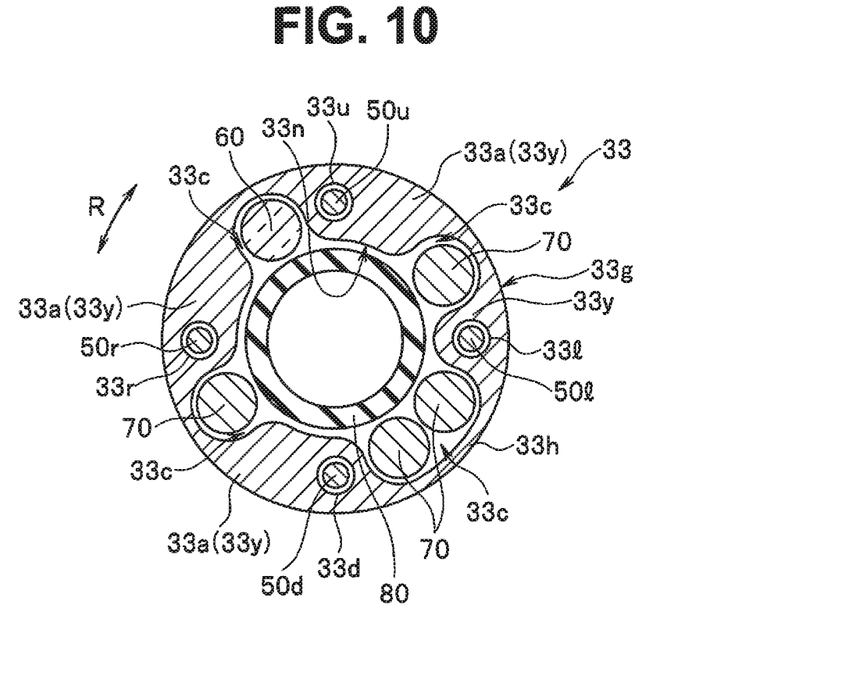
FIG. 10 is a cross-sectional view of a wall portion showing a modification of the thick wall portion different from FIGS. 6, 8 and 9.
Figure 11:
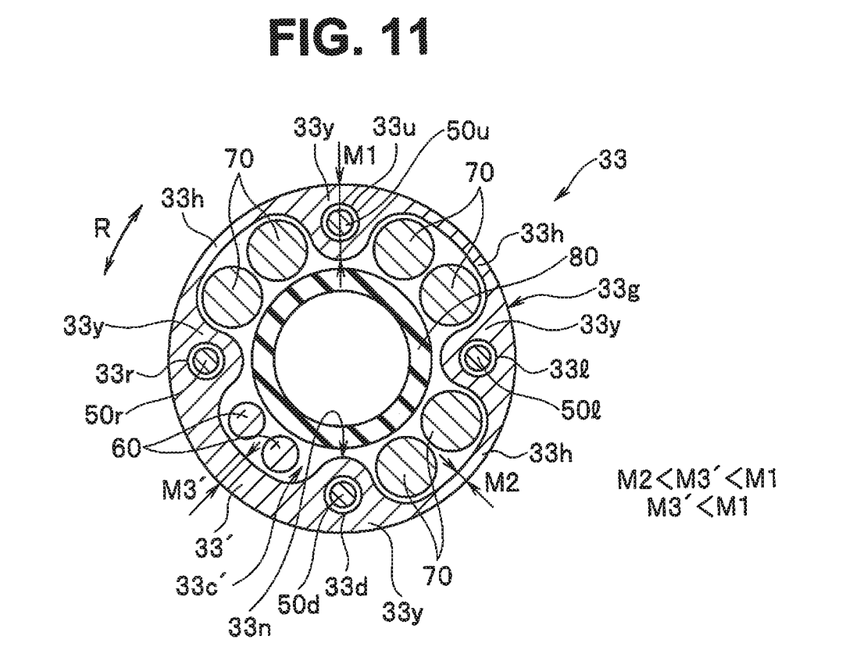
FIG. 11 is a cross-sectional view of a wall portion showing a modification of the thick wall portion different from FIGS. 6, 8, 9 and 10.

Note that a modification will be shown below with FIGS. 8 to 11. FIG. 8 is a cross-sectional view of a wall portion showing a modification of a thick wall portion in FIG. 6; FIG. 9 is a cross-sectional view of a wall portion showing a modification of the thick wall portion different from FIGS. 6 and 8; FIG. 10 is a cross-sectional view of a wall portion showing a modification of the thick wall portion different from FIGS. 6, 8 and 9; and FIG. 11 is a cross-sectional view of a wall portion showing a modification of the thick wall portion different from FIGS. 6, 8, 9 and 10.

The thick wall portion 33*a* is not limited to the position shown in FIGS. 5 and 6 described above. The thick wall portion 33*a* can be formed at various positions according to the shapes and number of internal components if the positions are on parts of the wall portion 33*m* different from the thin wall portions 33*h* between the plurality of wire inserting portions 33*y* in the direction-around-longitudinal-axis R.

For example, as shown in FIG. 8, a further thick wall portion 33*a* may be formed at a position facing the position of the thick wall portion 33*a* shown in FIG. 6 with the tube 80 interposed therebetween and positions surrounding the light guide 60.

Further, as shown in FIG. 9, the whole wall portion 33*m* may be formed as the thick wall portion 33*a* except for a space 33*c* through which the light guide 60 and the image pickup cable 70 are inserted.

Furthermore, as shown in FIG. 10, the thick wall portion 33*a* may be formed in a manner of surrounding the light guide 60 and the image pickup cable 70 in the spaces 33*c*.

Further, as shown in FIG. 11, a thick wall portion 33*a*' may be formed thinner than the thick wall portion 33*a* shown in FIG. 6 (M3'<M3; M2<M3'<M1). Note that the light guide 60 may be arranged in a space 33*c*' formed by the thick wall portion 33*a*'.

Note that the above configuration of the bending piece 33 applies to all of the bending pieces 31, 32, and 34 to 47.

In the configurations of bending piece as shown in FIGS. 8 to 11, effects similar to the effects of the present embodiment described above can be obtained.

Figure 12:
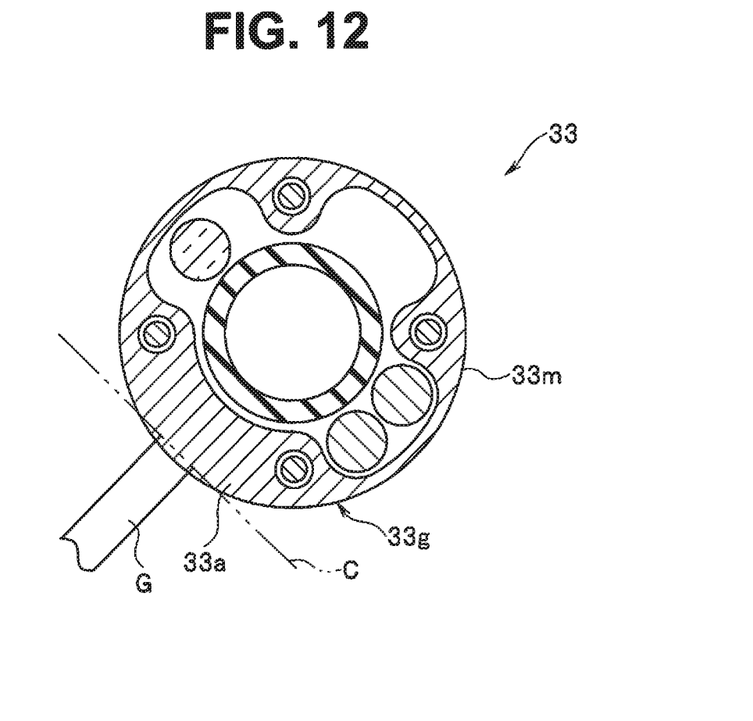
FIG. 12 is a cross-sectional view showing a modification in which a gate is provided on an outer peripheral surface of the thick wall portion in FIG. 6.
Figure 13:
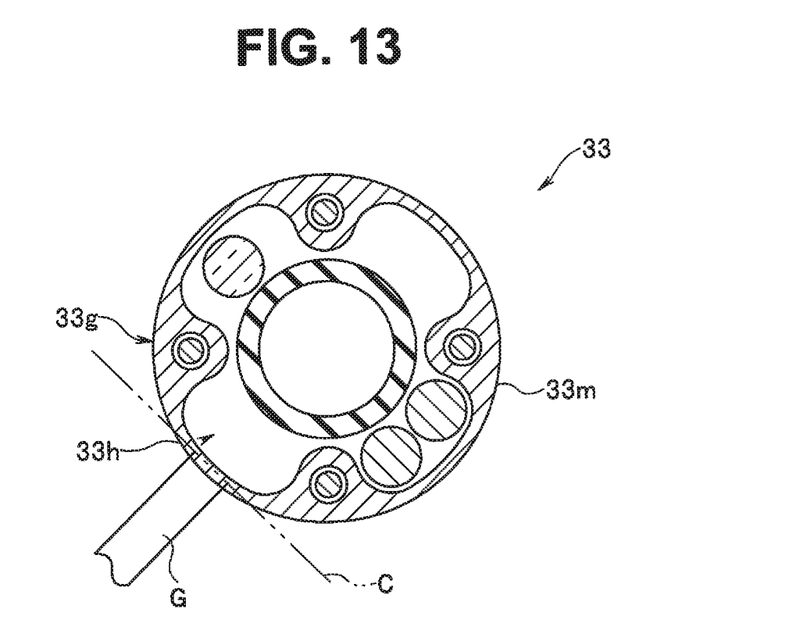
FIG. 13 is a cross-sectional view showing a modification in which a gate is provided on an outer peripheral surface of a thick wall portion in FIG. 7.

Other modifications will be further shown below with FIGS. 12 and 13. FIG. 12 is a cross-sectional view showing a modification in which a gate is provided on an outer peripheral surface of the thick wall portion in FIG. 6; and FIG. 13 is a cross-sectional view showing a modification in which a gate is provided on an outer peripheral surface in FIG. 7.

As shown in FIG. 12, a gate G used for MIM molding may be provided on the outer peripheral surface 33*g* of the thick wall portion 33*a* of the wall portion 33*m*.

In other words, the gate mark B may be a protruding portion that is projectingly provided on the outer peripheral surface 33*g* of the thick wall portion 33*a*.

Note that the protruding portion is removed for surface matching with the outer peripheral surface 33*g* by secondary processing after MIM molding.

According to the above, there is a possibility that, if the gate G is formed on the outer peripheral surface 33*g* of a thin wall portion 33*h* as shown in a conventional bending piece in FIG. 13, the thin wall portion 33*h* is broken at the time of performing gate cutting along a cut line C in FIG. 13.

However, if the gate G is formed on the outer peripheral surface 33g of the thick wall portion 33a as shown in FIG. 12, it is possible to prevent breakage of the wall portion 33m after gate cutting or deformation of the wall portion 33m in the secondary processing described above because the thick wall portion 33a is formed having the third thickness M3.

Further, since the gate G is provided on the outer peripheral surface 33g, the secondary processing for removing the gate mark G can be easily performed.

Note that the configuration of the bending piece 33 described above applies to all of the bending pieces 31, 32, and 34 to 47.

Though the bending portion 12 with the rivetless structure for bending in four directions has been shown as an example in the present embodiment described above, the present embodiment is not limited to the structure, and is certainly applicable to a rivetless structure for bending in two directions.

What is claimed is:

1. A bending portion for an endoscope, the bending portion comprising:
    a plurality of bending pieces having contact portions on end portions facing each other in a longitudinal axis direction, the contact portions being in contact with each other, the plurality of bending pieces being mutually rotatable and being consecutively provided in the longitudinal axis direction, wherein each of the bending pieces comprises an annular wall portion having an inner peripheral surface and an outer peripheral surface formed around a longitudinal axis and having a predetermined length in the longitudinal axis direction, wherein the annular wall portion comprising;
        a plurality of wire inserting portions in which the annular wall portion has a first wall thickness and through holes are formed, the through holes passing through the annular wall portion in the longitudinal axis direction, pulling wires configured to cause the bending pieces to rotate being inserted through the through holes;
        a thin wall portion having a second wall thickness thinner than the first wall thickness, the thin wall portion being formed in a plurality of first areas of the annular wall portion, each of the plurality of first areas being between first adjacent pairs of the plurality of wire inserting portions around the longitudinal axis; and
        a thick wall portion formed in a second area of the annular wall portion, the second area being between a second adjacent pair of the plurality of wire inserting portions around the longitudinal axis, the second adjacent pair being different from the first adjacent pairs, the second area being different from the first area, the thick wall portion having a third wall thickness that is equal to or less than the first wall thickness and is thicker than the second wall thickness;
    wherein an entirety of the second area between the second adjacent pair of the plurality of wire inserting portions is the thick wall portion formed to have the third wall thickness; and
    a gate mark of injection molding for molding the bending piece is formed on the thick wall portion.

2. The bending portion for endoscope according to claim 1, wherein the gate mark is a protruding portion that is projectingly provided on an end surface of the thick wall portion in the longitudinal axis direction.

3. The bending portion for endoscope according to claim 1, wherein an entirety of each of the plurality of first areas between the first adjacent pairs of the plurality of wire inserting portions is the thin wall portion formed to have the second wall thickness.

\* \* \* \* \*